(12) United States Patent
Yamamoto et al.

(10) Patent No.: US 9,586,241 B2
(45) Date of Patent: Mar. 7, 2017

(54) WASHING DEVICE AND WASHING METHOD

(71) Applicant: Sharp Kabushiki Kaisha, Osaka-shi, Osaka (JP)

(72) Inventors: Hiroaki Yamamoto, Yao (JP); Kohichi Tamura, Yao (JP); Yohichi Furukawa, Yao (JP); Tomoyuki Kanzaki, Yao (JP)

(73) Assignee: Sharp Kabushiki Kaisha, Sakai (JP)

( * ) Notice: Subject to any disclaimer, the term of this patent is extended or adjusted under 35 U.S.C. 154(b) by 21 days.

(21) Appl. No.: 14/378,999

(22) PCT Filed: Feb. 28, 2013

(86) PCT No.: PCT/JP2013/055576
§ 371 (c)(1),
(2) Date: Aug. 15, 2014

(87) PCT Pub. No.: WO2013/137013
PCT Pub. Date: Sep. 19, 2013

(65) Prior Publication Data
US 2015/0027502 A1    Jan. 29, 2015

(30) Foreign Application Priority Data
Mar. 14, 2012    (JP) ................. 2012-057639

(51) Int. Cl.
*B08B 3/00* (2006.01)
*B08B 3/12* (2006.01)
*B08B 3/08* (2006.01)

(52) U.S. Cl.
CPC ............. *B08B 3/12* (2013.01); *A61B 90/70* (2016.02); *B08B 3/08* (2013.01)

(58) Field of Classification Search
CPC .............. B08B 3/12; B08B 3/08; A61B 90/70
See application file for complete search history.

(56) References Cited

U.S. PATENT DOCUMENTS 5,425,815 A * 6/1995 Parker .................... A61B 1/123
134/2
6,379,614 B1 * 4/2002 Sergio ....................... A61L 2/18
422/109

(Continued)

FOREIGN PATENT DOCUMENTS

JP      05-192064 A    8/1993
JP   2000-176389 A    6/2000

(Continued)

OTHER PUBLICATIONS

Official Communication issued in International Patent Application No. PCT/JP2013/055576, mailed on Apr. 23, 2013.

*Primary Examiner* — Bibi Carrillo
(74) *Attorney, Agent, or Firm* — Keating & Bennett, LLP

(57) ABSTRACT

Provided are a washing device and a washing method that can remove burnt body fluid adhered to a medical instrument. The washing device can remove the burned component which adhered to a tip end portion of a surgical instrument by applying a physical force caused by the pressure of cleaning agent-dissolved water ejected from a cleaning nozzle member in addition to a chemical force caused by a cleaning agent contained in the cleaning agent-dissolved water.

3 Claims, 3 Drawing Sheets

(56) References Cited

U.S. PATENT DOCUMENTS

| | | | |
|---|---|---|---|
| 6,582,654 B1* | 6/2003 | Kral | A61B 1/123 |
| | | | 134/161 |
| 2002/0159917 A1 | 10/2002 | Swart et al. | |
| 2006/0289043 A1* | 12/2006 | Sasaki | A61B 90/70 |
| | | | 134/169 C |
| 2007/0231198 A1* | 10/2007 | Lin | A01N 25/16 |
| | | | 422/28 |
| 2008/0236631 A1 | 10/2008 | Lin et al. | |
| 2009/0025760 A1* | 1/2009 | Ciampaglia | A61B 19/34 |
| | | | 134/115 R |
| 2009/0241987 A1* | 10/2009 | Serizawa | B08B 3/12 |
| | | | 134/1 |
| 2013/0152982 A1* | 6/2013 | Tanaka | A61B 1/123 |
| | | | 134/115 R |
| 2015/0027502 A1* | 1/2015 | Yamamoto | A61B 19/34 |
| | | | 134/34 |

FOREIGN PATENT DOCUMENTS

| | | |
|---|---|---|
| JP | 2006-230795 A | 9/2006 |
| JP | 2007-130037 A | 5/2007 |
| JP | 2011-087737 A | 5/2011 |
| JP | 2011-240318 A | 12/2011 |

* cited by examiner

WASHING DEVICE AND WASHING METHOD

BACKGROUND OF THE INVENTION

The present invention relates to a washing device and a washing method that are provided for removing body fluid such as burnt blood adhered to a medical instrument.

BACKGROUND ART

In general, body fluid such as blood is attached to a medical instrument that is used during surgery. In a case of a medical instrument such as an electric scalpel of which the temperature becomes high, the attached body fluid is burned and firmly adheres to the medical instrument due to heat of the medical instrument. Similarly, in a case where the body fluid contacts with highly reactive chemicals such as acid, properties of the body fluid are changed and the body fluid firmly adheres to the medical instrument.

The body fluid firmly adheres to the medical instrument in this manner cannot be removed by a washer disinfector using a general cleaning agent. In Guidelines for Cleaning, 2010, published by the Japanese Society of Medical Instrumentation, it is described that "body fluid which is burned and adheres to an end of bipolar coagulation forceps cannot be removed by automatic cleaning". Moreover, in an operation in an actual medical site, for example, after soaking the medical instrument in an alkaline cleaning agent, brush cleaning is performed by human hands.

PTL 1, which is not about a washing device for medical instruments, describes a washing device for removing a burnt work piece which adheres to wire mesh during food processing.

CITATION LIST

Patent Literature

PTL 1: Japanese Unexamined Patent Application Publication No. 5-192064

BRIEF SUMMARY OF THE INVENTION

Technical Problem

Using the washing device described in PTL 1, cleaning of a medical instrument to which a burnt body fluid has firmly adhered is attempted. However, it is difficult to remove the body fluid. Currently, there is no proposed washing device that can remove the burnt body fluid.

Accordingly, as described above, in the actual medical site, the burnt body fluid adhered to the medical instrument is cleaned by human hands while being visually checked by a human. However, when the cleaning is performed by human hands, there is a possibility that the human hands may contact with the adhered body fluid, which may cause a risk of infection.

The present invention is made from the viewpoint of the above-described problem and an object of the present invention is to provide a washing device and a washing method that are provided for removing burnt body fluid adhered to a medical instrument.

Solution to Problem

The present invention provides a washing device for cleaning a medical instrument, in which burnt body fluid adhered to the medical instrument is removed in a non-contact state using a physical force and a chemical power of a cleaning agent.

It is preferable that the washing device of the present invention include a nozzle member which has a nozzle hole that ejects liquid containing the cleaning agent, in which the physical force is a pressure of the liquid ejected from the nozzle hole.

In the washing device of the present invention, it is preferable that a cleaning target portion of the medical instrument be disposed within the nozzle hole.

It is preferable that the washing device of the present invention include a cleaning tank which stores the liquid in which the medical instrument is immersed; and an ultrasonic wave generation unit which is provided with the cleaning tank and generates ultrasonic waves, in which the physical force is vibration caused by the ultrasonic waves.

In the washing device of the present invention, it is preferable that the cleaning agent have a function of decomposing a burnt protein component.

In the washing device of the present invention, it is preferable that the cleaning agent be an aqueous cleaning agent having surfactant as a main component.

In the washing device of the present invention, it is preferable that the cleaning agent contain sodium hydroxide or percarbonate.

It is preferable that the washing device of the present invention be configured to be able to collectively clean a plurality of medical instruments.

It is preferable that the washing device of the present invention include a fixing portion which fixes the medical instrument and is capable of fixing the medical instrument in a state of non-contacting the cleaning target portion of the medical instrument when fixing the medical instrument using human hands.

In addition, the present invention provides a washing method, in which a medical instrument is cleaned using the above-described washing device.

Advantageous Effects of Invention

According to the present invention, it is possible to remove the burnt body fluid adhered to the medical instrument in a non-contact state without using human hands.

According to the present invention, it is also possible to remove the burnt body fluid adhered to the medical instrument by ejecting a liquid containing a cleaning agent from a nozzle hole of a nozzle member.

According to the present invention, it is also possible to more certainly remove the burnt body fluid adhered to the medical instrument by arranging a cleaning target portion of the medical instrument within a nozzle hole of a nozzle member.

According to the present invention, it is also possible to remove the burnt body fluid adhered to the medical instrument by applying vibration, which is caused by ultrasonic waves generated by an ultrasonic wave radiation unit, to the medical instrument immersed in a liquid stored in a cleaning tank.

According to the present invention, the cleaning agent has a function of decomposing a burnt protein component, and therefore, it is possible to decompose a main component of the burnt body fluid, thereby more certainly removing the burnt body fluid adhered to the medical instrument.

According to the present invention, it is possible to remove dirt adhered to the medical instrument using surfactant.

According to the present invention, it is possible to more certainly remove the dirt adhered to the medical instrument using sodium hydroxide or percarbonate.

According to the present invention, it is possible to collectively clean a plurality of medical instruments using a single washing device.

According to the present invention, it is possible to fix and clean the medical instrument without human hands being in contact with the cleaning target portion of the medical instrument, and therefore, it is possible to reduce the risk of infection.

According to the present invention, it is possible to remove the burnt body fluid adhered to the medical instrument by using the washing device in a non-contact state without using human hands.

BRIEF DESCRIPTION OF DRAWINGS

The object, the features, and the advantage of the present invention will become clearer from the following detailed description and the accompanying drawings.

DETAILED DESCRIPTION OF THE INVENTION

Figure 1:
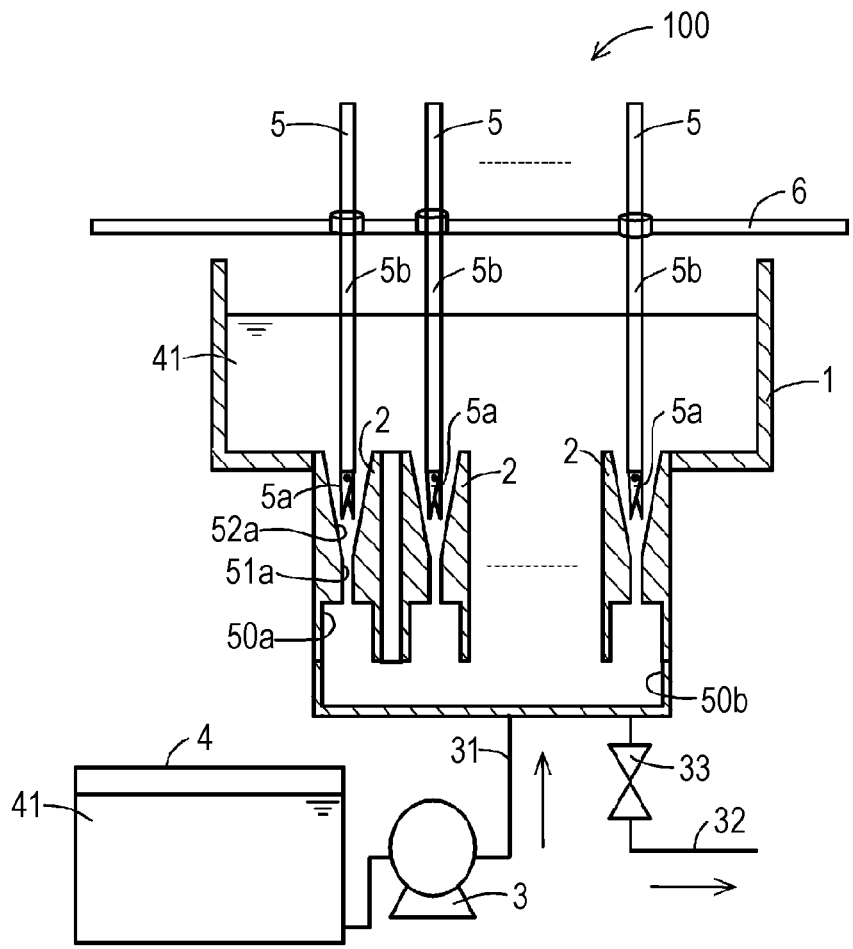
FIG. 1 is a diagram schematically illustrating a configuration of a washing device according to a first embodiment of the present invention.

FIG. 1 is a diagram schematically illustrating a configuration of a washing device 100 according to a first embodiment of the present invention. A washing method of the present invention can be realized using the washing device 100.

The washing device 100 is an apparatus for cleaning a medical instrument and removes burnt body fluid adhered to the medical instrument in a non-contact state using a physical force and a chemical force of a cleaning agent without using human hands.

An example of the medical instrument to be cleaned in the washing device 100 includes a surgical instrument 5 having a cutting or gripping part for performing endoscopic surgery provided at a tip end portion 5a. In particular, a burned and adhered body fluid, properties of which are changed through heat or chemicals, (hereinafter, referred to as a "burned component"), firmly adheres to a surgical instrument 5 such as an electric scalpel.

The washing device 100 of the present embodiment is configured to remove the burned component by applying a physical force caused by a jet generated from a cleaning nozzle member 2 in a state in which the tip end portion 5a of the surgical instrument 5 to which the above-described burned component firmly adheres is immersed in a cleaning agent.

The washing device 100 is configured to include a cleaning tank 1, a plurality of cleaning nozzle members 2, a booster pump 3, a storage tank 4 storing water in which a cleaning agent is dissolved (hereinafter referred to as "cleaning agent-dissolved water 41"), and a fixing tool 6 that fixes a surgical instrument 5.

The cleaning tank 1 and the storage tank 4 are connected to each other through a feed pipe 31. The booster pump 3 is connected to the feed pipe 31. The cleaning agent-dissolved water 41 stored in the storage tank 4 is pressure-fed, by operating the booster pump 3, through the inside of the feed pipe 31 in a pressurized state that, for example, $P=0.05$ MPa to 0.2 MPa, and is supplied to the inside of the cleaning tank 1. The cleaning agent-dissolved water 41 which is in the pressurized state and supplied to the inside of the cleaning tank 1 in this manner is ejected from a nozzle hole 21 of each of the plurality of cleaning nozzle members 2 disposed in the cleaning tank 1. The cleaning agent-dissolved water 41 ejected from the nozzle hole 21 of the cleaning nozzle members 2 forms a jet in the cleaning tank 1 and is held in a state of being stored in the cleaning tank 1.

Here, the flow rate of the cleaning agent-dissolved water 41 ejected from the nozzle hole 21 of each of the cleaning nozzle members 2 is set to be within a range of 35 L/min to 50 L/min.

Figure 2:
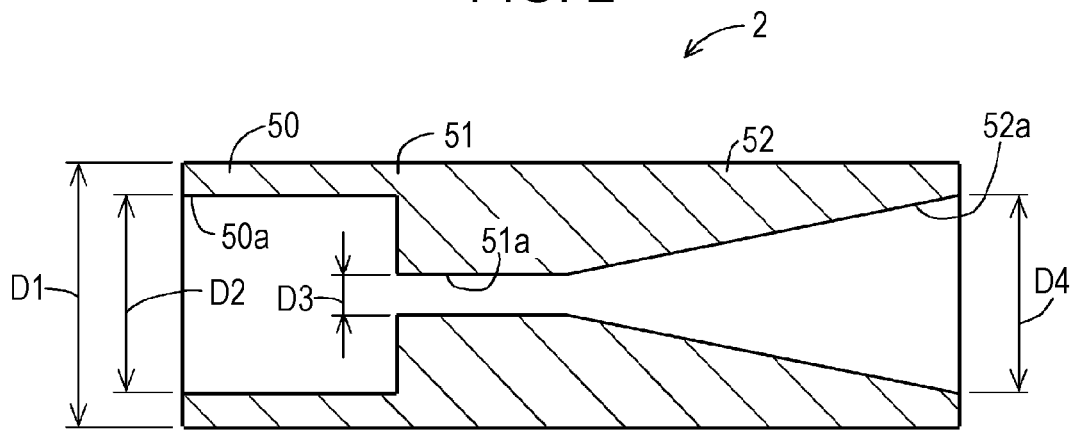
FIG. 2 is a diagram illustrating a configuration of a cleaning nozzle member.
Figure 3:
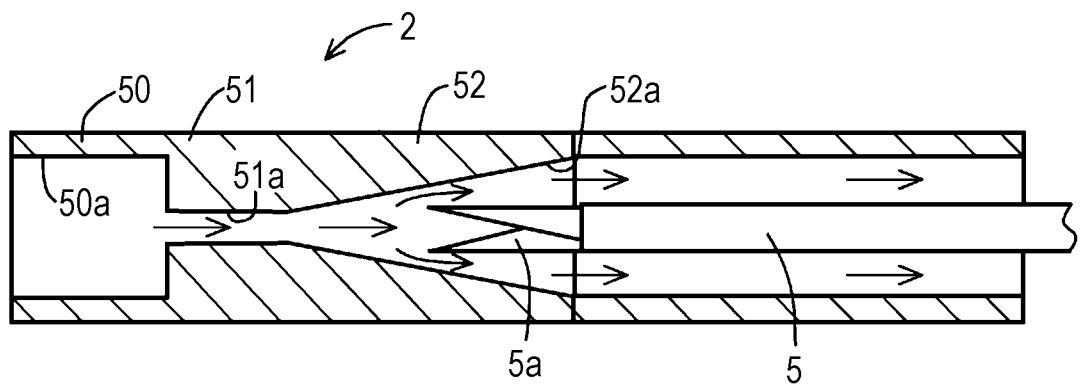
FIG. 3 is a diagram illustrating a state in which cleaning agent-dissolved water is ejected from the cleaning nozzle member.

FIG. 2 is a diagram illustrating a configuration of the cleaning nozzle member 2. FIG. 3 is a diagram illustrating a state in which the cleaning agent-dissolved water 41 is ejected from the cleaning nozzle member 2.

Each of the cleaning nozzle members 2 includes a supply unit 50 having a supply hole 50a to which the feed pipe 31 is connected and to which the cleaning agent-dissolved water 41 is supplied from the feed pipe 31; a throttle portion 51 having a throttle hole 51a as an orifice communicating with the supply hole 50a; and an ejection portion 52 having an ejection hole 52a communicating with the throttle hole 51a. The supply unit 50, the throttle portion 51, and the ejection portion 52 are integrally formed in this order by forming a common center axis and the supply hole 50a, throttle hole 51a, and the ejection hole 52a are formed by having an axis which is the same as the center axis.

Each of the supply holes 50a is defined by a cylindrical inner circumferential surface of the supply unit 50 and communicates with an inflow space 50b to which the feed pipe 31 is connected. The outer diameter D1 of the supply unit 50 is, for example, 35 mm and the inner diameter D2 thereof is, for example, 20 mm. The throttle hole 51a is defined by a cylindrical inner circumferential surface of the throttle portion 51. The inner diameter D3 of the throttle hole 51a is, for example, 6 mm. Furthermore, the ejection hole 52a is defined by a truncated conical inner circumferential surface of the ejection portion 52. The inner diameter of an inflow side opening portion, which communicates with the throttle hole 51a, of the ejection hole 52a is the same as the inner diameter D3 of the throttle hole 51a and the inner diameter D4 of an outflow side opening portion of the ejection hole 52a is, for example, 20 mm.

Since the cleaning nozzle member 2 is configured in this manner, the cleaning agent-dissolved water 41 pressure-fed to the supply hole 50a flows out to the inside of the ejection hole 52a through the throttle hole 51a in a state where the flow velocity V is increased to, for example, $V=20$ m/sec to 30 m/sec. Then, the cleaning agent-dissolved water becomes gas-liquid mixed fluid containing minute bubbles by cavitation and is used for cleaning the surgical instrument 5 which is a cleaning object inserted in the ejection hole 52a. The temperature T of the cleaning agent-dissolved water 41 released from the throttle hole 51a to the ejection hole 52a may be adjusted by heating the cleaning agent-dissolved water 41 using heating means such as a heating resistor at an upstream side of the throttle hole 51a, for example, in the supply hole 50a, so as to be, for example, 20° C. to 50° C. Accordingly, it is possible to further improve the cleaning effect.

Figure 4:
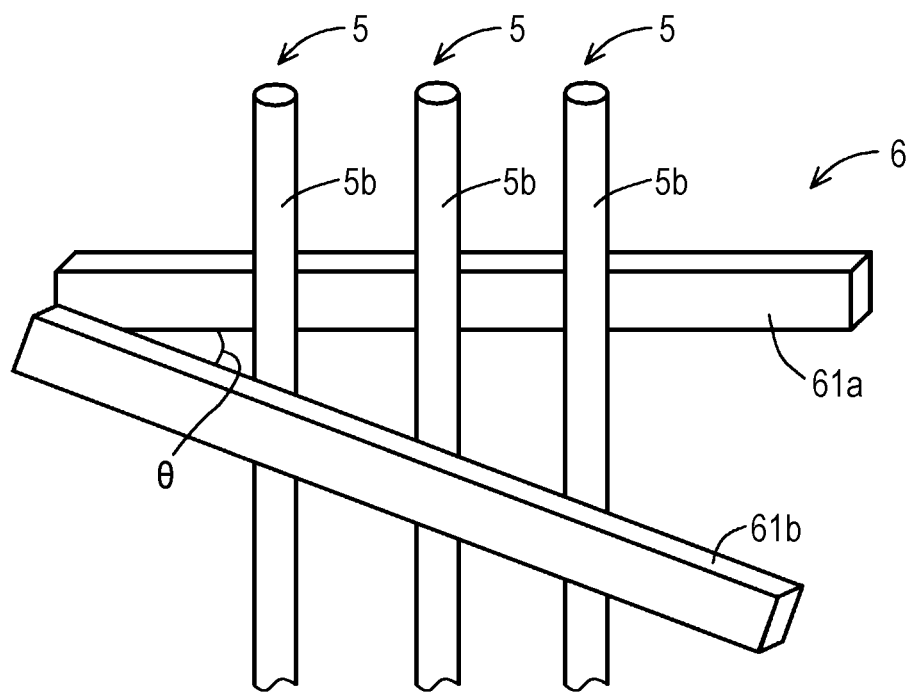
FIG. 4 is a diagram illustrating a configuration of a fixing tool.

FIG. 4 is a diagram illustrating a configuration of a fixing tool 6. The fixing tool 6 has a plurality of fixing portions 61a and 61b and is configured to fix a body portion 5b of the surgical instrument 5 to the fixing portions 61a and 61b. Each of the fixing portions 61a and 61b is formed of a long plate-like member having a rectangular cross section. One end portion of the fixing portion 61a in the longitudinal direction and one end portion of the fixing portion 61b in the longitudinal direction are fixed by forming a predetermined angle θ, for example, 15° to 30°, and the other end portions of the fixing portions 61a and 61b in the longitudinal direction are configured to be vertically separated as illustrated in FIG. 4. By inserting the body portions 5b of a plurality of (three in the present embodiment) surgical instruments 5 between the fixing portions 61a and 61b, the respective surgical instruments 5 are stably supported in a state of being slightly inclined with respect to a vertical direction by a reaction force against a rotational moment due to their own weights, and therefore, it is possible to maintain the surgical instruments 5 in a fixed state without being supported by human hands.

In addition, a drain pipe 32 is connected to the bottom of the cleaning tank 1 and an opening and closing valve 33 that opens and closes the channel of the drain pipe 32 is connected to the drain pipe 32. After finishing the cleaning treatment in the washing device 100, the used cleaning agent-dissolved water 41 in the cleaning tank 1 can be discarded to the outside of the device. When discarding the used cleaning agent-dissolved water 41 which is stored in the cleaning tank 1 to the outside of the device, the opening and closing valve 33 is released to make the cleaning agent-dissolved water 41 flow through the inside of the drain pipe 32.

In addition, a compound having a function of decomposing the burnt protein component is preferably used as the cleaning agent which is used in the washing device 100 of the present embodiment and contained in the cleaning agent-dissolved water 41. Examples of such a cleaning agent include surfactant, sodium hydroxide, percarbonate (bleach), bleach activators, chelating agents, and silver compounds. In addition, the concentration of the cleaning agent in the cleaning agent-dissolved water 41 is preferably set within a range of 2 wt % to 4 wt %. Furthermore, the pH of the cleaning agent-dissolved water 41 is preferably within a range of 9.8 to 10.3.

In the washing device 100 of the present embodiment, cleaning treatment is performed by ejecting the above-described cleaning agent-dissolved water 41 toward the tip end portion 5a of the surgical instrument 5 from the cleaning nozzle member 2, and therefore, it is possible to efficiently decompose the burned component which adheres to the tip end portion 5a by using a chemical force caused by the cleaning agent. Accordingly, it is possible to more certainly remove the burned component which adheres to the tip end portion 5a of the surgical instrument 5.

Figure 5:
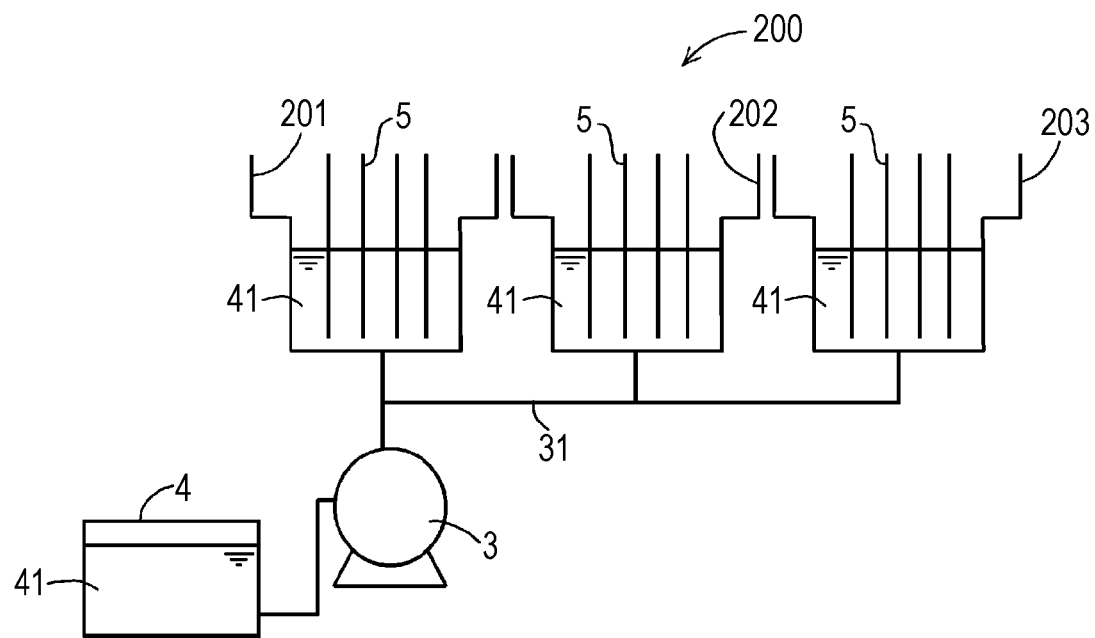
FIG. 5 is a diagram schematically illustrating a configuration of a washing device according to a second embodiment of the present invention.

FIG. 5 is a diagram schematically illustrating a configuration of a washing device 200 according to a second embodiment of the present invention. The washing device 200 resembles the washing device 100 of the above-described first embodiment, and the corresponding portions will be denoted by the same reference numerals as used above and the detailed description thereof will be omitted.

In the washing device 200, a plurality of cleaning tanks 201, 202, and 203, each of which is configured similarly to the cleaning tank 1 provided in the above-described washing device 100, are disposed in parallel. A plurality of the cleaning nozzle members 2 are provided in each of the cleaning tanks 201, 202, and 203 similarly to the cleaning tank 1.

Each of the cleaning tanks 201, 202, and 203 is connected to the storage tank 4 through the feed pipe 31. The booster pump 3 is connected to the feed pipe 31. The cleaning agent-dissolved water 41 stored in the storage tank 4 is pressure-fed through the inside of the feed pipe 31 in a pressurized state by operating the booster pump 3, and is supplied to the inside of the cleaning tanks 201, 202, and 203. The cleaning agent-dissolved water 41 which is in the pressurized state and supplied to the inside of the cleaning tanks 201, 202, and 203 in this manner is ejected from the plurality of cleaning nozzle members 2 disposed in the cleaning tanks 201, 202, and 203. The cleaning agent-dissolved water 41 is ejected from the cleaning nozzle members 2 disposed in the cleaning tanks 201, 202, and 203 and is jetted in the cleaning tanks 201, 202, and 203.

In the washing device 200 provided with the plurality of cleaning tanks 201, 202, and 203 arranged in parallel, it is possible to remove, in the cleaning tanks 201, 202, and 203, the burned component which adheres to the tip end portions 5a of the surgical instruments 5 using a physical force caused by the cleaning agent-dissolved water 41 ejected from the cleaning nozzle members 2 and using a chemical force caused by the cleaning agent. In such washing device 200, it is possible to perform the cleaning treatment on a plurality of surgical instruments 5 by suppressing the deterioration of the ejection force of the cleaning agent-dissolved water 41 from the cleaning nozzle member 2 in the cleaning tanks 201, 202, and 203.

Figure 6:
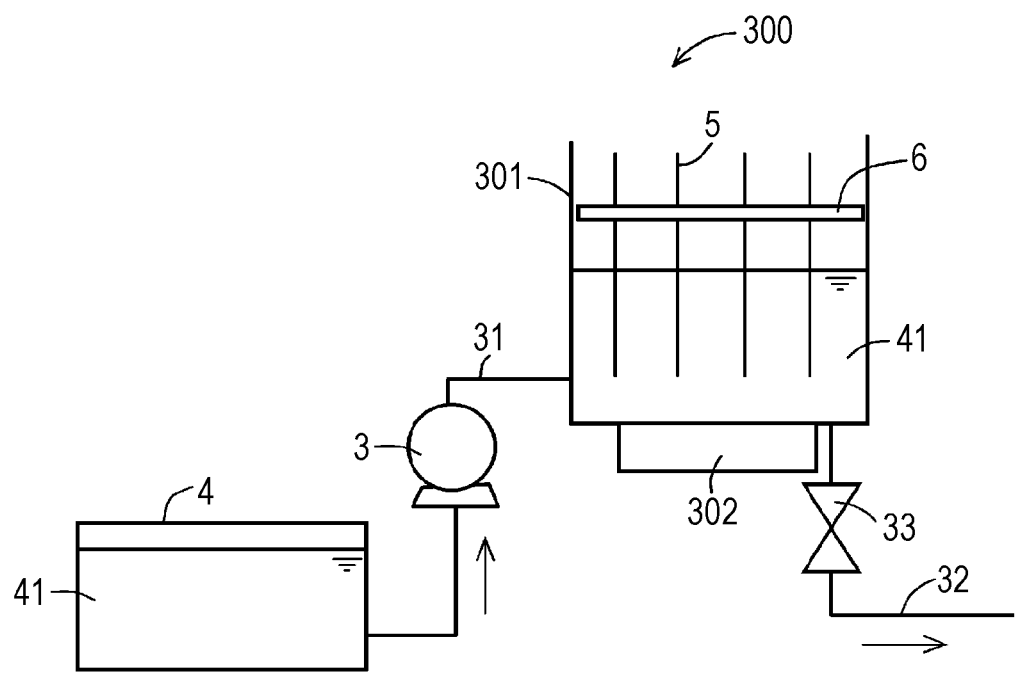
FIG. 6 is a diagram schematically illustrating a configuration of a washing device according to a third embodiment of the present invention.

FIG. 6 is a diagram schematically illustrating a configuration of a washing device 300 according to a third embodiment of the present invention. The washing device 300 resembles the washing device 100 of the above-described first embodiment, and the corresponding portions will be denoted by the same reference numerals as used above and the detailed description thereof will be omitted.

The washing device 300 is configured to remove the burned component adhered to the tip end portion 5a of the surgical instrument 5 by applying vibration caused by ultrasonic waves as a physical force.

The washing device 300 is configured to have a cleaning tank 301 that stores the cleaning agent-dissolved water 41 and an ultrasonic wave generation unit 302. In the washing device 300, ultrasonic waves are generated by the ultrasonic wave generation unit 302 in a state where a plurality of surgical instruments 5 fixed by the fixing tool 6 are immersed in the cleaning agent-dissolved water 41 stored in the cleaning tank 301. Accordingly, it is possible to apply a physical force caused by ultrasonic vibration to the surgical instruments 5 immersed in the cleaning agent-dissolved water 41 stored in the cleaning tank 301. Therefore, it is possible to remove the burned component which adheres to the tip end portions 5a of the surgical instruments 5 by using a physical force caused by the ultrasonic vibration and using a chemical force caused by the cleaning agent.

In the washing device 300 of the present embodiment, the ultrasonic wave generation unit 302 generates ultrasonic waves having a frequency of 34 kHz to 37 kHz. The ultrasonic wave generation unit 302 applies vibration to the burned component which adheres to the tip end portion 5*a* of the surgical instrument 5 by generating the ultrasonic waves in the above-described frequency band and facilitates separation of the burned component from the surface of the tip end portion 5*a* of the surgical instrument 5, and therefore, it is possible to efficiently remove the burned component.

In addition, the temperature of the cleaning agent-dissolved water 41 stored in the cleaning tank 301 may be adjusted by heating the cleaning agent-dissolved water using heating means such as a heating resistor so as to be within a range of, for example, 20° C. to 50° C. Accordingly, it is possible to further improve the cleaning effect.

EXAMPLES

Hereinafter, the present invention will be described in more detail with reference to Examples. However, the Examples are merely examples of the embodiment of the present invention and do not limit the present invention.

<Production of Surgical Instrument to which Burned Component Adhered>

A surgical instrument for performing endoscopic surgery was prepared. Simulated blood was applied to a tip end portion of the surgical instrument and the simulated blood was brought into contact with a 25 W soldering iron for electronic parts for 10 seconds to 20 seconds to create a state where the simulated blood was burned and adhered to the surgical instrument. The surgical instrument to which the burned component adhered was produced in this manner.

<Preparation of Cleaning Agent-Dissolved Water>

[Cleaning Agent-Dissolved Water A]

Cleaning agent-dissolved water A containing 20 wt % of sodium hydroxide was prepared by dissolving the sodium hydroxide in pure water. The pH of the cleaning agent-dissolved water A was 14.

[Cleaning Agent-Dissolved Water B]

Weak alkaline cleaning agent-dissolved water B with a pH of 9.8 was prepared as a cleaning agent by dissolving higher alcohol nonionic surfactant, percarbonate, bleach activators, chelating agents, or silver compounds in pure water.

Example 1

A surgical instrument to which a burned component adhered was subjected to cleaning treatment using the washing device 100 provided with the cleaning nozzle member as illustrated in FIG. 1. Cleaning agent-dissolved water used in the cleaning treatment was the above-described cleaning agent-dissolved water A. The flow rate of the cleaning agent-dissolved water A which was pressure-fed in a pressurized state at a pressure of 0.1 MPa and ejected from the cleaning nozzle member (inner diameter of a throttle hole was 6 mm) at a flow velocity of 14.7 m/sec was set to 25 L/min, and the cleaning time was 15 minutes. The temperature of the cleaning agent-dissolved water A was 25° C.

Example 2

A surgical instrument to which a burned component adhered was subjected to cleaning treatment similarly to Example 1 except that the above-described cleaning agent-dissolved water B was used as the cleaning agent-dissolved water and the cleaning time was 30 minutes.

Example 3

A surgical instrument to which a burned component adhered was subjected to cleaning treatment using the washing device 300 provided with the ultrasonic wave generation unit as illustrated in the drawing. The cleaning agent-dissolved water used in the cleaning treatment was the above-described cleaning agent-dissolved water A, ultrasonic waves having a frequency of 35 kHz and an output of 300 W were generated by the ultrasonic wave generation unit, and the cleaning time was 15 minutes. The temperature of the cleaning agent-dissolved water A was 25° C.

Example 4

A surgical instrument to which a burned component adhered was subjected to cleaning treatment similarly to Example 3 except that the above-described cleaning agent-dissolved water B was used as the cleaning agent-dissolved water and the cleaning time was 30 minutes.

Comparative Example 1

A surgical instrument to which a burned component adhered was subjected to cleaning treatment similarly to Example 1 except that the liquid ejected from the cleaning nozzle member was pure water (pH 6.5) and the cleaning time was 30 minutes.

Comparative Example 2

A surgical instrument to which a burned component adhered was subjected to cleaning treatment similarly to Example 3 except that the liquid for immersion was pure water (pH 6.5) and the cleaning time was 30 minutes.

Comparative Example 3

The cleaning treatment was performed similarly to Example 1 except that the cleaning agent-dissolved water A was not ejected from the cleaning nozzle member and a surgical instrument to which a burned component adhered was immersed in the cleaning agent-dissolved water A for 30 minutes in the cleaning tank.

Comparative Example 4

The cleaning treatment was performed similarly to Example 2 except that the cleaning agent-dissolved water B was not ejected from the cleaning nozzle member and a surgical instrument to which a burned component adhered was immersed in the cleaning agent-dissolved water B for 30 minutes in the cleaning tank.

The removability of the burned component adhered to the surgical instrument was visually evaluated in the above-described Examples 1 to 4 and Comparative Examples 1 to 4. A case where the burned component was completely removed was evaluated as "good" indicating good cleaning treatment capability, a case where most of the burned component was removed while a very small portion thereof remained was evaluated as "fair" indicating comparatively good cleaning capability, and a case where it was confirmed that most of the burned component remained was evaluated as "poor" indicating insufficient cleaning treatment capability. The evaluation results are shown in Table 1.

TABLE 1

|  | Washing device | Cleaning agent-dissolved water | Evaluation Result |
| --- | --- | --- | --- |
| Example 1 | Washing device 100 | Cleaning agent-dissolved water A | good |
| Example 2 | Washing device 100 | Cleaning agent-dissolved water B | good |
| Example 3 | Washing device 300 | Cleaning agent-dissolved water A | good |
| Example 4 | Washing device 300 | Cleaning agent-dissolved water B | fair |
| Comparative Example 1 | Washing device 100 | Water | poor |
| Comparative Example 2 | Washing device 300 | Water | poor |
| Comparative Example 3 | No application of physical force | Cleaning agent-dissolved water A | poor |
| Comparative Example 4 | No application of physical force | Cleaning agent-dissolved water B | poor |

As is clear from the results of Table 1, in Examples 1 to 4 to which the physical force caused by the pressure of the cleaning agent-dissolved water ejected from the cleaning nozzle member or the physical force of the ultrasonic vibration caused by the ultrasonic wave generation unit was applied in addition to the chemical force caused by the cleaning agent, it was possible to remove the burned component which adhered to the surgical instrument.

The present invention can be implemented in various other modes without departing from the spirit or the main features thereof. Accordingly, the above-described embodiments are merely examples in all respects and the scope of the present invention is indicated in the claims and is not bound by any of the text of the specification. Furthermore, all of the modification or the alteration belonging to the claims is within the scope of the present invention.

REFERENCE SIGNS LIST 1, 201, 202, 203, 301 Cleaning tanks
2 Cleaning nozzle member
3 Booster pump
4 Storage tank
5 Surgical instrument
6 Fixing tool
41 Cleaning agent-dissolved water
100, 200, 300 Washing device
302 Ultrasonic wave generation unit

The invention claimed is:

1. A washing device for cleaning a medical instrument, the washing device comprising:
a nozzle including a nozzle hole that ejects liquid to apply pressure to a cleaning target portion of the medical instrument, and
a fixing tool including at least one fixing portion, the at least one fixing portion including a plate-shaped member; wherein
the cleaning target portion is a portion of the medical instrument to be cleaned,
the pressure includes a physical force exerted by the liquid ejected from the nozzle hole; and
the at least one fixing portion fixes a portion other than the cleaning target portion of the medical instrument during cleaning such that the cleaning target portion of the medical instrument is disposed within the nozzle hole but does not contact any portion of the nozzle hole or the nozzle such that the cleaning target portion is contacted only by the liquid ejected from the nozzle hole.

2. The washing device according to claim 1, further comprising:
a cleaning tank which stores the liquid in which the medical instrument is immersed; and
an ultrasonic wave generator which is provided with the cleaning tank and generates ultrasonic waves,
wherein the physical force includes vibration caused by the ultrasonic waves.

3. The washing device according to claim 1,
wherein the washing device is structured to collectively clean a plurality of medical instruments.

* * * * *